(12) United States Patent
De Vries et al.

(10) Patent No.: US 8,178,323 B2
(45) Date of Patent: May 15, 2012

(54) EMULSIFIER PREPARED USING A GLYCOSYL TRANSFERASE

(75) Inventors: Hendrik Jan De Vries, Sellingen (NL); Cindy Semeijn, Groningen (NL); Pieter Lykle Buwalda, Groningen (NL)

(73) Assignee: Coöperatie AVEBE U.A., Veendam (NL)

( * ) Notice: Subject to any disclaimer, the term of this patent is extended or adjusted under 35 U.S.C. 154(b) by 628 days.

(21) Appl. No.: 11/995,131

(22) PCT Filed: Jul. 10, 2006

(86) PCT No.: PCT/NL2006/000347
§ 371 (c)(1),
(2), (4) Date: Mar. 25, 2009

(87) PCT Pub. No.: WO2007/008066
PCT Pub. Date: Jan. 18, 2007

(65) Prior Publication Data
US 2010/0029928 A1    Feb. 4, 2010

(30) Foreign Application Priority Data
Jul. 12, 2005    (EP) .................................... 05076605

(51) Int. Cl.
C12P 19/14    (2006.01)
C12P 19/44    (2006.01)
C12Q 1/48    (2006.01)
C12Q 1/40    (2006.01)

(52) U.S. Cl. ................. 435/99; 435/15; 435/22; 435/74

(58) Field of Classification Search .................... 435/15, 435/22, 74, 99
See application file for complete search history.

(56) References Cited

U.S. PATENT DOCUMENTS

| | | | |
|---|---|---|---|
| 3,238,064 A * | 3/1966 | Royal et al. ................... | 127/69 |
| 3,565,887 A | 2/1971 | Parmerter et al. | |
| 4,035,235 A | 7/1977 | Richards et al. | |
| 4,835,105 A * | 5/1989 | Seres et al. ..................... | 435/97 |
| 5,594,125 A * | 1/1997 | Seyschab et al. ............. | 536/103 |
| 5,776,476 A | 7/1998 | Billmers et al. | |
| 5,854,225 A | 12/1998 | Richard et al. | |
| 5,935,826 A * | 8/1999 | Blue et al. ...................... | 435/96 |
| 2003/0092804 A1 * | 5/2003 | Detering et al. ............. | 524/107 |

FOREIGN PATENT DOCUMENTS

| | | |
|---|---|---|
| EP | 0332027 A1 | 9/1989 |
| EP | 0418945 A1 | 3/1991 |
| EP | 0690170 A1 | 1/1996 |
| EP | 0806434 A1 | 11/1997 |
| EP | 0913406 A1 | 5/1999 |
| EP | 1149845 A2 | 10/2001 |
| JP | 4081403 | 3/1992 |
| WO | WO8901043 A1 | 2/1989 |
| WO | WO9213962 A1 | 8/1992 |
| WO | WO9424169 A1 | 10/1994 |
| WO | WO9815347 A1 | 4/1998 |
| WO | 0042076 | 7/2000 |
| WO | 0058445 | 10/2000 |
| WO | WO0116348 A1 | 3/2001 |
| WO | WO03/002728 A2 | 1/2003 |

OTHER PUBLICATIONS

Przylas et al, J. Mol. Biol., vol. 296, pp. 873-886 (2000).*
Van der Maarel et al, J. Biotechnol., vol. 94, pp. 137-155 (2002).*

* cited by examiner

*Primary Examiner* — Robert T. Crow
(74) *Attorney, Agent, or Firm* — Hoffmann & Baron, LLP

(57) ABSTRACT

The invention relates to an emulsifier, a method for preparing said emulsifier, and to its use in various applications, primarily food and cosmetic applications. The invention also relates to the use of said emulsifier for the creation of an elastic, gelled foam. An emulsifier according to the invention is based on a starch which is enzymatically converted, using a specific type of enzyme, and modified in a specific esterification reaction.

17 Claims, No Drawings

EMULSIFIER PREPARED USING A GLYCOSYL TRANSFERASE

This application is the U.S. National Phase of, and Applicants claim priority from, International Application Number PCT/NL2006/000347 filed 10 Jul. 2006 and European Application bearing Serial No. 05076605.4 filed 12 Jul. 2005, which are incorporated herein by reference.

BACKGROUND OF THE INVENTION

The invention relates to an emulsifier, a method of preparing said emulsifier, and to its use in various applications, primarily food and cosmetic applications.

Many products encountered in daily life, particularly food and cosmetic products, are examples of colloidal systems. Colloidal systems are characterized by the presence of small particles of solids, liquids or gases homogeneously distributed throughout the volume of a carrier. The particles are often referred to as the dispersed or discontinuous phase of a colloidal system, whereas the carrier is typically referred to as the continuous phase. Typical examples of colloidal systems include ice cream and bread, in which the dispersed phase consists of small air bubbles, and salad dressings in which the dispersed phases is composed of small droplets of liquid oil dispersed in an aqueous, liquid continuous phase.

A colloidal system wherein both the dispersed and the continuous phase are liquids is classified as an emulsion. An emulsion is an intimate mixture of two immiscible liquids wherein one liquid phase is dispersed in the other in the form of small droplets. Traditional emulsions are classified according to the composition of the phases. If the continuous phase is water and the discontinuous phase is oil, the emulsion is classified as an oil-in-water (O/W) emulsion. The reversed situation is referred to as water-in-oil (W/O) emulsion. Generally, O/W emulsions are white and creamy, while W/O emulsions are of darker colour and have a greasy texture.

All colloidal systems, including emulsions, have in common that they typically require stabilization to prevent separation into two phases. There are different stabilization requirements for solid and liquid emulsions. For example, in a fat spread such as margarine, the W/O emulsion is essentially stabilized by crystallized fat in a three dimensional network. A liquid emulsion system is a more dynamic system. When oil is vigorously stirred in water, a crude form of an emulsion is formed. This emulsion will be highly unstable; the system will separate into oil and water layers within a short period of time. It is for stabilizing that emulsifiers are used.

Various chemical products and compositions are used in the food and cosmetic industries as emulsifiers. In many functions, the emulsifiers also function as stabilizer of the viscosity or fluidity of the continuous phase of the emulsion. Typically, it is desired that the emulsion is shelf-stable and the emulsifier may assist in achieving that goal.

Gum arabic is preferred in many applications for its shelf-stability, particularly in refrigerated or frozen storage of emulsions. It has been used as an emulsifier and stabilizer in foods such as confections, syrups, flavour oil emulsions, ice cream and beverages. It is a branched, substituted heteropolysaccharide characterized by extreme water solubility, low viscosity, and the absence of odour, colour and flavour. It is a naturally occurring gum produced in the Middle East and Africa. It is, however, an expensive product and its supply and quality are unpredictable.

In many applications, alkyl or alkenyl succinated starches can replace gum arabic. Particularly, octenyl succinated starches have found wide spread use as emulsifier. Use of these starches can reduce costs and improve stability in supply.

Starch in itself is not suitable for use as an emulsifier because it lacks the necessary lipophilic groups. It is therefore not compatible with systems comprising water-insoluble substances. Amphiphilic characteristics can be introduced in starch by treating it with a cyclic dicarboxylic acid anhydride, like octenyl succinic anhydride, to form an alkyl or alkenyl dicarboxylic starch. As a result of this modification, the starch is stabilized in aqueous solutions, so that retrogradation will be hindered. A significant advantage of these starches is that their hydrophilicity is retained, while hydrophobicity is introduced.

For many applications, there is an ongoing need for further improvements in emulsion stability, and thus for improved emulsifiers. It is in this context that the present invention was made.

SUMMARY OF THE INVENTION

The invention provides an emulsifier having improved emulsion stabilizing properties. In particular, the invention provides an emulsifier emulsifier comprising a hydrophobic starch, obtained by etherification, esterification or amidation of a starch with a hydrophobic reagent and enzymatic conversion using a glycosyl transferase (E.C.2.4), wherein the hydrophobic reagent comprises an alkyl or alkenyl chain having from 7-24 carbon atoms. Not only can an emulsifier according to the invention be used for stabilizing emulsions, composed of two immiscible liquid phases, but it can also be employed to stabilize other types of colloidal systems, most notably foams composed of a gaseous dispersed phase in a liquid, oil or water, continuous phase. Other advantages of the invention will become clear from the following detailed description and the appended examples.

DETAILED DESCRIPTION OF THE INVENTION

It is to be noted that it has been proposed in the prior art to treat an octenyl succinated starch with different enzymes.

In the European patent application 0 913 406 the use of a glucoamylase is proposed. It is stated that the use of this enzyme preferably leads to degradation of the starch to such an extent that not an emulsifying agent but an encapsulating agent is obtained. In accordance with the present invention, such degradation is not desired.

The European patent application 0 332 027 discloses the use of a beta-amylase. It is noted, however, that 55% of the product obtained has a dextrose equivalent (DE) of about 50 (maltose). The rest of the product is a stable, so-called beta-limit dextrin. This implies that for emulsification only about 45% of the obtained product can be used as it is well-known that products having a DE of more than 20 are insufficiently capable of stabilizing an emulsion.

The starch on which an emulsifier according to the invention is based can, in principle, be derived from any botanical source. Both root or tuber starches, such as cassava or potato starch, and cereal and fruit starches, such as maize, rice, wheat or barley starches can be used. Legume starches, such as pea or bean starches, can also be used.

Natural starches typically have a more or less fixed ratio of the two components of starch, amylose and amylopectin. Of some starches, such as maize or rice starch, a natural occurring variety exists which contains essentially only amylopectin. These starches, which are normally called waxy starches, can also be used. Of other starches, such as potato or cassava starch, there are genetically modified or mutant varieties which also essentially only contain amylopectin. It will be understood that the use of these varieties, typically comprising more than 80 wt. %, preferably more than 95 wt. %, based on dry weight of the starch, of amylopectin, is also within the scope of the invention. Finally, also starch varieties which are high in amylose, such as high amylose potato starch, can be used for the preparation of an emulsifier according to the invention. In accordance with the invention, starches of all amylose to amylopectin ratios may be used.

In order to prepare an emulsifier according to the invention, the starch must undergo two treatments. It has to be subjected to enzymatic conversion with a glycosyl transferase (E.C.2.4) and it has to be reacted with a hydrophobic reagent. It has been found possible to perform these treatments in any order in order to achieve good product qualities. When the starch is first treated with the enzyme and then reacted with the hydrophobic reagent, it has been found possible to achieve a higher degree of substitution (DS) in the hydrophobation which leads to greater stabilizing capacity in emulsions. Also, if the starch is treated in this order, a more homogeneous product is typically obtained. On the other hand, when the starch is first reacted with the hydrophobic reagent and then subjected to the action of the enzyme, a purer product is obtained which requires relatively few purification and washing treatments.

The enzyme which is used for enzymatically converting the starch in accordance with the invention is a glycosyl transferase of the class E.C.2.4. Preferred enzymes are those belonging to the class of hexosyltransferases (E.C.2.4.1).

In accordance with one preferred embodiment of the invention, the starch is treated in an aqueous medium with an enzyme from the class of 4-α-glucanotransferases (E.C.2.4.1.25), or an enzyme of which the activity corresponds to said enzyme. The typical and relevant activity of an enzyme of this class is that it transfers a segment of a 1,4-α-D-glucan to a new 4-position in an acceptor, which may be a glucose or a 1,4-α-D-glucan, as for example disclosed in EP-A-0 932 444.

A 4-α-glucanotransferase can be obtained from various organisms. From literature it is known that these enzymes occur in representatives of the eukarya and the bacteria. It is further known that these enzymes are present in representatives of the archae baceteria. It is preferred that a 4-α-glucanotransferase is used which is resistant to rather high temperatures, e.g. a temperature of about 70° C. Typical examples include 4-α-glucanotransferases from *Thermus thermophilus, Thermotoga maritima*, and from thermophilic representatives of the archae bacteria. However, also non-thermostable 4-α-glucanotransferases from, e.g., the potato or *Escherichia coli*, respectively D-enzyme and amylomaltase, can be used. The 4-α-glucanotransferase should be free of α-amylase activity which can readily be achieved by those skilled in the art by for instance purification.

In accordance with another preferred embodiment of the invention, the starch is treated in an aqueous medium with an enzyme from the class of cyclomaltodextrin glucanotransferases (E.C.2.4.1.19), or an enzyme of which the activity corresponds to said enzyme. This type of enzyme cyclizes part of a 1,4-α-D-glucan chain by formation of a 1,4-α-D-glucosidic bond, as for example disclosed in WO-A-89/01043, WO-A-92/13962, and EP-A-0 690 170.

A cyclomaltodextrin glucanotransferase can be obtained from various sources, such as disclosed in R. L. Whistler et al., "Starch: Chemistry and Technology", 2nd Ed., 1984, Academic Press, pp. 143-144, D. Duchêne, "Minutes of the Fifth International Symposium on Cyclodextrins", Editions de Santé, Paris 1990, pp. 19-61, and A. R. Hedges, "Minutes of the Sixth International Symposium on Cyclodextrins", Editions de Sante, Paris, 1992, pp. 23-58.

In accordance with yet another preferred embodiment of the invention, the starch is treated in an aqueous medium with an enzyme from the class of 1,4-α-glucan branching enzymes (E.C.2.4.1.18), or an enzyme of which the activity corresponds to said enzyme. This type of enzyme transfers a segment of a 1,4-α-D-glucan chain to a primary hydroxyl group in a similar glucan chain, as for example disclosed in EP-A-0 690 170.

A 1,4-α-glucan branching enzyme can originate from many sources, for instance from bacteria of the species *Bacillus stearothermophilus*. A specific example of such a 1,4-α-glucan branching enzyme is disclosed in EP-A-0 418 945.

The enzymatic conversion can be carried out both with gelatinized starch and with starch which is still in granular form, but has been brought into a swollen state, i.e. in partially gelatinized state. It is preferred, however, that the starch is in gelatinized condition. Gelatinization can be carried out batchwise or continuously in a steam injection device (e.g. a jet-cooker). The enzyme can be added before or, and this is preferred, after gelatinization.

The reaction conditions for carrying out the enzymatic conversion will depend on the type of starch and glycosyl transferase used and can be easily determined by those skilled in the art, for example based on the above referenced publications concerning 4-α-glucanotransferases, cyclomaltodextrin glucanotransferases, and 1,4-α-glucan branching enzymes. In practice, this is usually done at or near a pH and temperature at which the enzyme has optimum activity and stability. The amount of enzyme used is not particularly critical and will primarily depend on the time which is desirably allocated for the conversion.

The progress of the enzymatic conversion can, again depending on the type of enzyme chosen, be followed by measuring viscosity or gel strength. Typically, the enzymatic conversion is stopped when a situation of equilibrium is reached, and no further conversion takes place.

After the desired enzymatic conversion has taken place, the enzyme may be deactivated, if desired, for instance by heating the reaction mixture. In case the enzymatic conversion was carried out using a partially gelatinized starch, gelatinization may reach completion upon deactivating the enzyme by heating. If desired, the enzyme can be removed from the starch by known separation techniques, such as dialysis.

In accordance with the invention, a hydrophobic substituent is attached to a starch by an ether, ester or amide linkage.

When the hydrophobic group is attached to the starch via an ether linkage, the hydrophobic reagent preferably comprises a halide, halohydrin, epoxide or glycidyl group as reactive site. The alkyl chain of the agent can vary from 4-24 carbon atoms, preferably from 7-20 carbon atoms. Suitable examples of hydrophobic reagents to provide an ether linkage are cetyl bromide, lauryl bromide, butylene oxide, epoxidized soybean fatty alcohols, epoxydized linseed fatty alcohols, allyl glycidyl ether, propyl glycidyl ether, butyl glycidyl ether, decane glycidyl ether, lauryl glycidyl ether, lauryl phenyl glycidyl ether, myristoyl glycidyl ether, cetyl glycidyl ether, palmityl glycidyl ether, stearyl glycidyl ether, linolyl glycidyl ether and mixtures thereof. Other etherification agents which may be used to react with starch in accordance with the invention are alkyl halides containing at least four carbon atoms, such as 1-bromodecane, 10-bromo-1-decanol, and 1-bromododecane.

In one embodiment of the invention, a charged hydrophobic group is introduced. A hydrophobic cationic group can be attached via an ether linkage by reaction of the starch with a reagent comprising a quaternary ammonium group, for example a 1-chloro-2-hydroxypropyltrialkyl ammonium salt or a glycidyltrialkyl ammonium salt. The alkyl chains of this quaternary ammonium group can vary from 1-24 carbon atoms, preferably from 7-20 carbon atoms, wherein at least one of the alkyl chains of the quaternary ammonium group comprises 4-24 carbon atoms. Preferably, the other alkyl chains have less than 7 carbon atoms. For example 1-chloro-2-hydroxypropyldimethyllauryl ammonium salt, 1-chloro-2-hydroxypropyldimethylmyristoyl ammonium salt, 1-chloro-2-hydroxypropyldimethylcetyl, 1-chloro-2-hydroxypropyldimethylstearyl, glycidyldimethyllauryl ammonium salt, glycidyldimethylmyristoyl ammonium salt, glycidyldimethylcetyl ammonium salt, glycidyldimethylstearyl ammonium salt, dialkylaminoethyl halide, or mixtures of the above can be applied as hydrophobic cationization reagent. A hydrophobic cationic group may be introduced by reaction with tertiary ammonium groups such as chloroethyldialkylamine hydrogen chloride salt. The alkyl chain of this tertiary ammonium group may vary from 1 to 24 carbon atoms. The reaction for introducing the hydrophobic cationic group may be performed analogous to the procedure disclosed in EP-A-0 189 935. A hydrophobic anionic group can be attached applying a 2-chloro-aminodialkyl acid as reagent, for instance analogous to the procedure disclosed in EP-A-0 689 829.

When the hydrophobic group is attached to the starch via an ester linkage, several kinds of reagents, such as alkyl anhydrides can be applied. The alkyl chain can vary from 4-24 carbons, preferably from 7-20 carbons. Especially, mixed anhydrides as octanoic acetic anhydride, decanoic acetic anhydride, lauroyl acetic anhydride, myristoyl acetic anhydride are suitable alkyl anhydrides.

In a preferred embodiment of the invention, hydrophobic anionic groups may be attached to the amylopectin starch. This may be accomplished by reaction of the specific starch with an alkyl succinic anhydride or alkenyl succinic anhydride. The alkyl chain can vary from 4-24 carbons, preferably from 7-20 carbons. Octenyl succinic anhydride, nonyl succinic anhydride, decyl succinic anhydride, dodecenyl succinic anhydride are most commonly applied. The esterification reaction to introduce the desired alkyl or alkenyl succinate groups can be performed in any known manner, for instance analogous to the procedure disclosed in U.S. Pat. No. 5,776,476. Preferably, the starch is reacted with an alkyl or alkenyl succinic anhydride comprising an alkyl or alkenyl group having from 8-12 carbon atoms. Octenyl succinic anhydride, nonyl succinic anhydride, decyl succinic anhydride, dodecenyl succinic anhydride are particularly preferred, while the highest preference is for octenyl succinic anhydride. Accordingly, the alkyl or alkenyl succinated starch preferably is octenyl succinated, nonyl succinated, decyl succinated, or dodecenyl succinated starch, even more preferably octenyl succinated starch.

For the preparation of a hydrophobic group linked to carboxymethyl amylopectin starch by an amide group the procedure as described in WO-A-94/24169 can analogously be applied. Examples of suitable reagents for introduction of an amide group include fatty amines comprising saturated or unsaturated hydrocarbon groups having from 8 to 30 carbon atoms. Branched hydrocarbon groups are not excluded, but linear chains are preferred. Preferably, the fatty radical originates from a $C_{12}$ to $C_{24}$ fatty amine. Particularly favorable results are obtained if the fatty amine is selected from the group consisting of n-dodecylamine, n-hexadecylamine, n-octadecylamine, cocoamine, tallowamine, hydrogenated N-tallow-1,3-diaminopropane, N-hydrogenated tallow-1,3-diaminopropane, and N-oleyl-1,3-diaminopropane. Such fatty amines are known under the trade names Armeen and Duomeen (AKZO Chemicals).

The degree of hydrophobic substitution, i.e. DS, defined as the average number of moles of hydrophobic substituents per mole glucose units, achieved in a process according to the invention, may vary particularly depending upon the envisaged application of the product. Generally, the DS will be greater than zero, preferably from 0.005 to about 0.5, more preferably from 0.01 to 0.1. It is surprising to note that even a very small DS leads to a relatively large effect.

The reaction with the hydrophobic reagent can be carried out in a suspension of the starch, i.e. using starch which is not pre-gelatinized, in a suspension of the starch, or under semi-dry conditions. When hydrophobation is carried out after the enzymatic conversion, the starch will typically already be gelatinized.

Preferably, water is used as a solvent when the reaction is performed in suspension or solution. When the used hydrophobic reagent has a low solubility in water, combinations of water and suitable water mixable organic solvents may be employed. Suitable organic solvents include, but are not limited to, methanol, ethanol, i-propanol, n-propanol, t-butanol, sec-butanol, methylethylketon, tetrahydrofuran, dioxan, and acetone. The reaction in solution is preferably performed using a reaction mixture comprising more than 20 wt. % of the starch and less than 80 wt. % of the solvent. More preferably, the starch content in the reaction mixture lies between 20 and 40 wt. %, whereas the solvent content preferably lies between 80 and 60 wt. %. If desired, the solution may be concentrated and/or purified, e.g. using dialysis, ultrafiltration, ultracentrifugation, or the like. An autoclave in combination with a dryer (drum dryer; spray dryer) may be used as a reaction vessel. The reaction is further performed under conditions which are well-known for analogous reactions. The pH lies preferably between 7 and 13. Preferably, a method according to the invention is performed in the presence of a caustic catalyst, such as an alkali metal hydroxide or the like. In accordance with specific embodiments, the caustic catalyst is used in such amounts that it is in fact present as a reagent.

An emulsifier according to the invention can be used in many applications, particularly in the food and cosmetics industry. It will be understood that the invention also encompasses the use of an emulsifier as described above for stabilizing emulsions, as well as food and cosmetic products comprising an emulsion or having the form of an emulsion, wherein the above described emulsifier is present as an emulsifier. An emulsifier according to the invention can be used in cosmetics as emulsifier, thickener, or surface active agent in for instance hair conditioners, shampoos, emollients, lotions, and creams.

In a preferred embodiment, an emulsifier according to the invention can be used to replace emulsifiers based on proteins, such as casein or caseinates, or other emulsifiers, such as glycerol monostearate or glycerol distearate, or to replace eggs in bakery products or in emulsified sauces. It is worthwhile noting that an emulsifier according to the invention is typically more versatile in this respect as it retains its emulsifying properties even at elevated temperatures, whereas egg yolk denaturates at temperatures in excess of 65° C. Also, the use of an emulsifier according to the invention reduces the risk of introducing bacteria which are often present in eggs, such as *salmonella*.

It has further been found that an emulsifier according to the invention can be used to create an elastic, gelled foam, particularly when based on a starch having a high amylose content. In accordance with this embodiment, it is preferred to use a starch having a high amylose content, such as from 20-70 wt. %, more preferably 30-50 wt. %, based on dry weight of the starch. Such a foam can be prepared by vigorously mixing starch in water in an amount of, e.g., 20 wt. % based on the weight of the mixture. Such foams can find application in both the food and cosmetic industries, e.g. as foam booster in for example whipped creams, meringues, shampoos, shaving creams, bath or shower gels, and liquid soaps.

In another embodiment, an emulsifier according to the invention may be used in papermaking. A preferred application in this regard is the use of an emulsifier according to the invention for stabilizing alkenyl succinic anhydride (ASA) and/or alkenyl ketene dimer (AKD) emulsions. Another preferred application is this regard is the use of an emulsifier according to the invention in emulsion polymerization of vinyl monomers, leading to emulsions which can be used in surface sizing or coating paper.

The invention will now be elucidated by the following, non-restrictive examples.

Example 1

The Preparation of an Octenyl Succinilated Additionally Branched Starch

A suspension of 5 mole regular potato starch in water (20% dry matter) was jet cooked at a temperature of 160° C. An amount of the solution corresponding with 250 g starch (dry substance) was transferred into a double walled glass reactor of 5 L and the temperature was set at 65° C. The pH was adjusted to 6.5 and 200 U enzyme (*Rhodothermus Marinus* branching enzyme, supplier TNO Food—Groningen) per gram starch was added. The reaction was allowed to proceed at 65° C. with constant mixing for 48 hours.

Then the solution is cooled to 30° C. and the pH of the solution was set at 8.5 by addition of an aqueous 4.4 wt. % NaOH solution. To the solution the octenyl succinic anhydride was added slowly in an amount to obtain a Dsmax of 0.028. During the addition the pH of the reaction mixture was kept constant at 8.5. After 4 hours reaction the mixture was neutralized to pH 6.2

The products were flocculated using ethanol. A blender was filled with 800 ml ethanol (95%). 200 ml starch solution was added slowly while the blender is mixing at 50% of its maximal velocity. Then the mixing speed was increased to full speed for 30 seconds and the mixture was filtered using a Büchner funnel. The product was resuspended in 800 ml ethanol, mixed at full speed, filtered and dried.

Example 2

The Preparation of an Octenyl Succinilated Amylomaltase Starch

A suspension (20% dry matter) containing 10 moles of regular potato starch in water was jet cooked at a temperature of 160° C. Then the amount of dry substance in the solution was calculated by measuring the mass and the concentration (brix %) of the solution. The solution was transferred into a double walled glass reactor of 10 L and the temperature was set at 70° C. The pH was adjusted to 6.2 and 2 U enzyme (Amylomaltase, supplier TNO Food—Groningen) per gram starch was added. The reaction was allowed to proceed at 70° C. with constant mixing for 24 hours. The enzyme was then deactivated by jet cooking the solution at a temperature of 160° C. Again the amount of dry substance in the solution was calculated by measuring the mass and the concentration (brix %) of the solution.

Then the solution is cooled to 30° C. and the pH of the solution was set at 8.5 by addition of an aqueous 4.4 wt. % NaOH solution. To the solution the octenyl succinic anhydride was added slowly in an amount to obtain a Dsmax of 0.028. During the addition the pH of the reaction mixture was kept constant at 8.5. After 4 hours reaction the mixture was neutralized to pH 6.2 and the solutions were spray dried using an inlet temperature of 220° C. and an outlet temperature of 103° C.

Example 3

The Preparation of an Amylomaltase Treated Octenyl Succinylated Starch

A starch suspension 39% (W/W) containing 15 moles of potato starch having an amylose content of 36 wt. %, was prepared in tap water and the pH of the suspension was set at 8.5 by the addition of an aqueous 4.4 wt. % NaOH solution. The temperature was set at 20° C. and to the solution the octenyl succinic anhydride was added slowly in an amount to obtain a Dsmax of 0.02. During the reaction the pH was maintained at 8.5 using 4.4% NaOH (W/V). After 4 hours reaction the mixture was neutralized to pH 6.2 and washed with 15 L tap water using a Büchner funnel. The products were drum dried as a 36% (W/W) suspension at 8 bar and 6 rpm (4 rolls, slit width 0.3 mm) and Grinded (Peppink, 250 µm sieve).

Then 10 moles of the drum dried octenyl succinilated starches were dissolved in a 10% concentration (W/W) in tap water in a stirred Terlet reactor at a temperature of 70° C. For a homogeneous solution, the paste was stirred for at least 4 hours before the enzyme was added. The pH of the solution was set at 6.2 and 2 units enzyme (Amylomaltase, supplier TNO Food—Groningen per gram starch (dry substance) was added. The reaction was stopped after 24 hours by jet cooking the solution at 160° C. After this the solution was spray dried using an inlet temperature of 220° C. and an outlet temperature of 103° C.

Example 4

Emulsifying Properties

Products were prepared as described in the examples 1-3. 6 grams of the starches were suspended in 10 ml sunflower oil and 190 ml of a 0.02% sodium azide solution was added. Pre-emulsions were prepared using the Silverston homogeniser at the maximum velocity for 1 minute. After these emulsions were prepared using the micro-fluidiser according to the scheme in table 1. The results are summarized in table 2.

TABLE 1

| Homogenisation using the micro-fluidiser | | |
|---|---|---|
| Cycle | Restrictions | Pressure (bars) |
| 1 | 0 | <50 |
| 2 | 2 | 400 |
| 3 | 2 | 400 |

TABLE 2

Stability of emulsions

| Emulsifier | Stable for | DS | DE |
|---|---|---|---|
| Alpha-amylase treated octenyl succinic derivative of potato starch | 3 days | 0.022 | 4.4 |
| Debranched octenyl succinic derivative of potato starch | 13 days | 0.021 | 6.5 |
| Amylomaltase treated octenyl succinic derivative of potato starch | 20 days | 0.018 | <0.5 |
| Additionally branched octenyl succinic derivative of potato starch | 34 days | 0.018 | <0.5 |
| Alpha-amylase treated octenyl succinic derivative of medium high amylose potato starch | 2 days | 0.023 | 3.9 |
| Amylomaltase treated octenyl succinic derivative of medium high amylose potato starch | 20 days | 0.023 | <0.5 |
| Alpha-amylase treated octenyl succinic derivative of amylopectin potato starch | 6 days | 0.021 | 4.7 |
| Additionally branched octenyl succinic derivative of amylopectin potato starch | 41 days | 0.019 | <0.5 |

Table 2 shows that the additionally branched- and the amylomaltase treated octenyl succinic derivatives of the starches can develop more stable emulsions. The degree of substitution (DS) was measured by saponification and acid-base titration; the dextrose equivalent (DE) was measured according to Luff-Schoorl.

Example 5

Foam Test 40 g of the products described in examples 1-3 and 160 g of demi water is whipped for 2-3 minutes at maximum velocity in the Hobart mixer using the whisks. The mixing time varies between 2 and 3 minutes and is depending on the foam development of the product.

The amylomaltase treated octenyl succinic derivative of medium high amylose potato starch developed an elastic gelled foam. The blank of medium high amylose potato starch developed a somewhat crumble gelled foam.

The invention claimed is:

1. A method of preparing an emulsifier comprising a hydrophobic starch, said method comprising etherification, esterification or amidation of a starch with a hydrophobic reagent comprising an alkyl or alkenyl chain having from 7-24 carbon atoms and enzymatic conversion using a glycosyl transferase (E.C.2.4).

2. A method according to claim 1, the starch is esterified with a hydrophobic reagent comprising an alkyl or alkenyl group having from 7 to 24 carbon atoms.

3. A method according to claim 1, wherein the starch is first subjected to enzymatic conversion with glycosyl transferase (E.C.2.4), followed by esterification with the alkyl or alkenyl succinic anhydride.

4. A method according to claim 1, wherein the starch is first esterified with the alkyl or alkenyl succinic anhydride, followed by enzymatic conversion with glycosyl transferase (E.C.2.4).

5. A method according to claim 1, wherein the hydrophobic starch is an alkyl or alkenyl succinated starch.

6. A method according to claim 5, wherein the alkyl or alkenyl succinated starch is octenyl succinated, nonyl succinated, decyl succinated, or dodecenyl succinated starch.

7. A method according to claim 6, wherein the starch is an octenyl succinated starch.

8. A method according to claim 1, wherein the degree of substitution (DS) of the alkyl or alkenyl succinated starch is from 0.005 to 0.5.

9. A method according to claim 1, wherein the degree of substitution (DS) of the alkyl or alkenyl succinated starch is from 0.01 to 0.1.

10. A method according to claim 1, wherein the glycosyl transferase is a 4-α-glucanotransferase (E.C.2.4.1.25).

11. A method according to claim 1, wherein the glycosyl transferase is a cyclomaltodextrin glucanotransferase (E.C.2.4.1.19).

12. A method according to claim 1, wherein the glycosyl transferase is a 1,4-α-glucan branching enzyme (E.C.2.4.1.18).

13. A method according to claim 1, wherein the starch is a potato, cassava, wheat, barley, maize, rice, pea, or bean starch.

14. A method according to claim 13, wherein the starch has an amylose content of from 20-70 wt. %, based on dry weight of the starch.

15. A method according to claim 14, wherein the starch has an amylose content of from 30-50 wt. %, based on dry weight of the starch.

16. A method according to claim 13, wherein the starch has an amylopectin content higher than 80 wt. %, based on dry weight of the starch.

17. A method according to claim 16, wherein the starch has an amylopectin content higher than 95 wt. %, based on dry weight of the starch.

* * * * *